(12) United States Patent
Veith

(10) Patent No.: US 7,824,389 B2
(45) Date of Patent: Nov. 2, 2010

(54) DISPOSABLE ABSORBENT UNDERGARMENT FOR MALES

(75) Inventor: Jerome S. Veith, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1600 days.

(21) Appl. No.: 10/693,555

(22) Filed: Oct. 24, 2003

(65) Prior Publication Data

US 2005/0090790 A1 Apr. 28, 2005

(51) Int. Cl.
*A61F 13/15* (2006.01)
*A61F 13/20* (2006.01)

(52) U.S. Cl. .................................. 604/385.23
(58) Field of Classification Search ............ 604/385.01, 604/385.29, 402
See application file for complete search history.

(56) References Cited

U.S. PATENT DOCUMENTS

| | | | |
|---|---|---|---|
| 3,559,648 A | 2/1971 | Mason, Jr. | |
| 3,766,922 A | 10/1973 | Krusko | |
| 3,926,189 A | 12/1975 | Taylor | |
| 4,037,602 A | 7/1977 | Hawthorne | |
| 4,326,302 A | 4/1982 | Lowe et al. | |
| 4,501,587 A | 2/1985 | Enloe | |
| 4,585,448 A | 4/1986 | Enloe | |
| 4,655,760 A | 4/1987 | Wisneski et al. | |
| 4,673,402 A | 6/1987 | Weisman et al. | |
| 4,762,521 A | 8/1988 | Roessler et al. | |
| 4,834,735 A | 5/1989 | Alemany et al. | |
| 4,846,827 A | 7/1989 | Thorson et al. | |
| 4,935,022 A | 6/1990 | Lash et al. | |
| 5,019,068 A | 5/1991 | Perez et al. | |

(Continued)

FOREIGN PATENT DOCUMENTS

EP 0 321 980 A2 6/1989

(Continued)

OTHER PUBLICATIONS

Pending U.S. Appl. No. 09/825,609, filed Apr. 3, 2001, 24 pages.

(Continued)

*Primary Examiner*—Melanie J Hand
(74) *Attorney, Agent, or Firm*—H. Michael Kubicki

(57) ABSTRACT

A disposable absorbent garment includes a body chassis having a terminal front waist edge, a terminal back waist edge longitudinally spaced from the terminal front waist edge, a first length defined between the terminal front waist edge and the terminal back waist edge, and a laterally extending centerline defined half way between the terminal front and back waist edges. An absorbent insert is fixedly secured to the body chassis. The absorbent insert has a retention region including an absorbent material. The retention region has first and second longitudinally spaced boundaries and a second length defined between the first and second boundaries. The second length is less than or equal to 50% of the first length, and at least 70% of the second length is positioned between the centerline and the terminal front waist edge. There is no absorbent material disposed outside of the retention region defined between the first and second boundaries. In one embodiment, the body chassis is formed from separate front and rear body panels. A method of assembling a disposable absorbent garment is also provided.

23 Claims, 2 Drawing Sheets

U.S. PATENT DOCUMENTS

| | | | |
|---|---|---|---|
| 5,047,023 | A | 9/1991 | Berg |
| 5,147,345 | A | 9/1992 | Young et al. |
| 5,262,223 | A | 11/1993 | Palumbo et al. |
| 5,348,547 | A | 9/1994 | Payne et al. |
| 5,376,198 | A | 12/1994 | Fahrenkrug et al. |
| 5,451,442 | A | 9/1995 | Pieniak et al. |
| 5,462,537 | A | 10/1995 | Carr et al. |
| 5,527,300 | A | 6/1996 | Sauer |
| 5,558,659 | A | 9/1996 | Sherrod et al. |
| 5,624,420 | A | 4/1997 | Bridges et al. |
| 5,695,488 | A | 12/1997 | Sosalla |
| 5,836,930 | A * | 11/1998 | Lantz et al. ............... 604/378 |
| 5,853,402 | A | 12/1998 | Faulks et al. |
| 6,217,563 | B1 * | 4/2001 | Van Gompel et al. . 604/385.101 |
| 6,364,863 | B1 | 4/2002 | Yamamoto et al. |
| 6,367,089 | B2 | 4/2002 | Van Gompel et al. |
| 6,409,712 | B1 | 6/2002 | Dutari |
| 6,423,042 | B1 | 7/2002 | Sasaki |
| 6,437,214 | B1 * | 8/2002 | Everett et al. ............... 604/378 |
| 6,488,670 | B1 | 12/2002 | Schild et al. |
| 6,497,695 | B1 | 12/2002 | Bruemmer-Prestley et al. |
| 6,497,696 | B1 | 12/2002 | Freiburger et al. |
| 6,500,161 | B1 | 12/2002 | Freiburger et al. |
| 6,500,162 | B1 | 12/2002 | Freiburger et al. |
| 6,503,239 | B1 | 1/2003 | Bruemmer-Prestley et al. |
| 6,508,799 | B1 | 1/2003 | Freiburger et al. |
| 6,514,235 | B1 | 2/2003 | Freiburger et al. |
| 6,720,471 | B1 * | 4/2004 | Arndt et al. ............... 604/367 |
| 2003/0066122 | A1 | 4/2003 | Niedermeyer |
| 2005/0027267 | A1 * | 2/2005 | Van Dyke et al. ........... 604/367 |

FOREIGN PATENT DOCUMENTS

| | | |
|---|---|---|
| EP | 0 321 985 A2 | 6/1989 |
| EP | 0 573 521 B1 | 4/1997 |
| EP | 0 630 221 B2 | 11/2000 |
| EP | 1 077 054 A2 | 2/2001 |
| EP | 1 084 687 A2 | 3/2001 |
| EP | 0 790 814 B1 | 2/2002 |
| GB | 2 263 859 A | 8/1993 |
| JP | 11-348221 A | 12/1999 |
| WO | WO 00/02510 A2 | 1/2000 |
| WO | WO 00/02511 A1 | 1/2000 |
| WO | WO 00/35395 A2 | 6/2000 |
| WO | WO 02/24011 A1 | 3/2002 |
| WO | WO 02/069843 A2 | 9/2002 |
| WO | WO 02/069868 A1 | 9/2002 |
| WO | WO 02/069871 A1 | 9/2002 |
| WO | WO 02/087634 A2 | 11/2002 |
| WO | WO 03/003960 A2 | 1/2003 |
| WO | WO 03/059223 A1 | 7/2003 |

OTHER PUBLICATIONS

Pending U.S. Appl. No. 10/274,503, filed Oct. 18, 2002, 33 pages.
Pending U.S. Appl. No. 10/325,500, filed Dec. 19, 2002, 33 pages.
International Search Report in corresponding International Application No. PCT/US2004/011722, dated Sep. 10, 2004, 11 pages.
International Search Report in International Application No. PCT/US03/18169, dated Sep. 8, 2004, 8 pages.

* cited by examiner

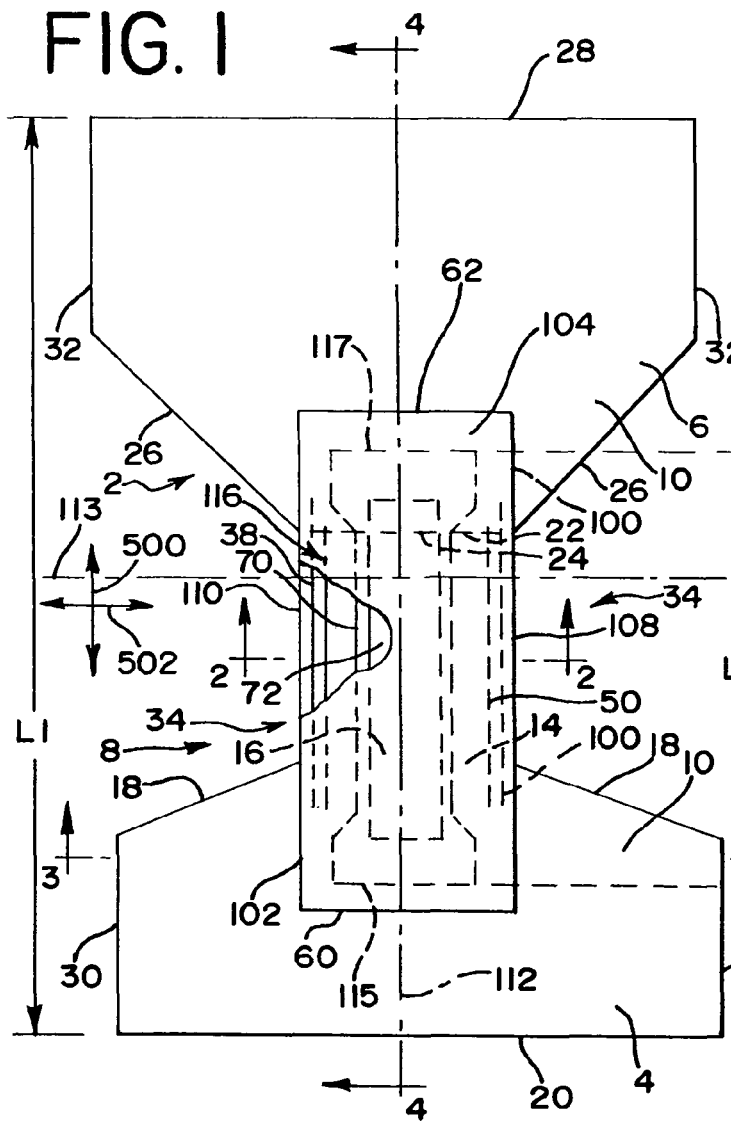
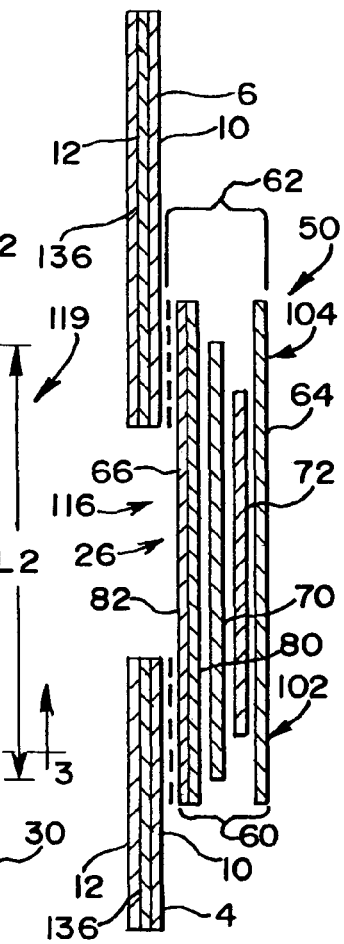
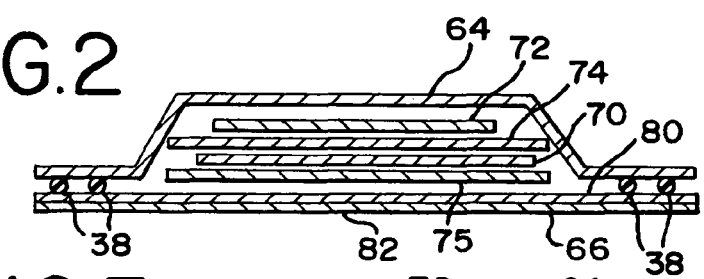
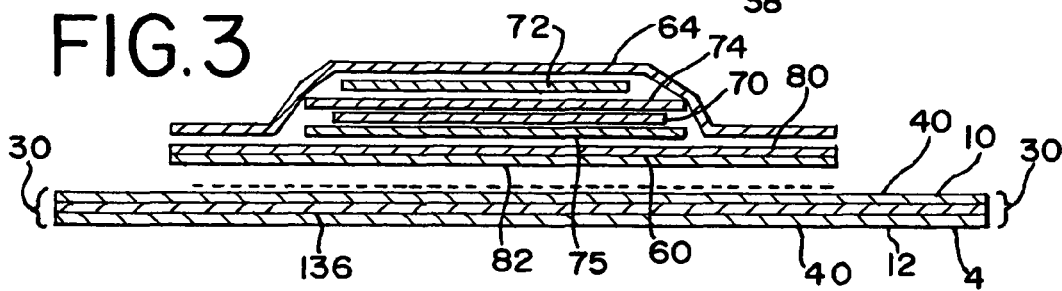

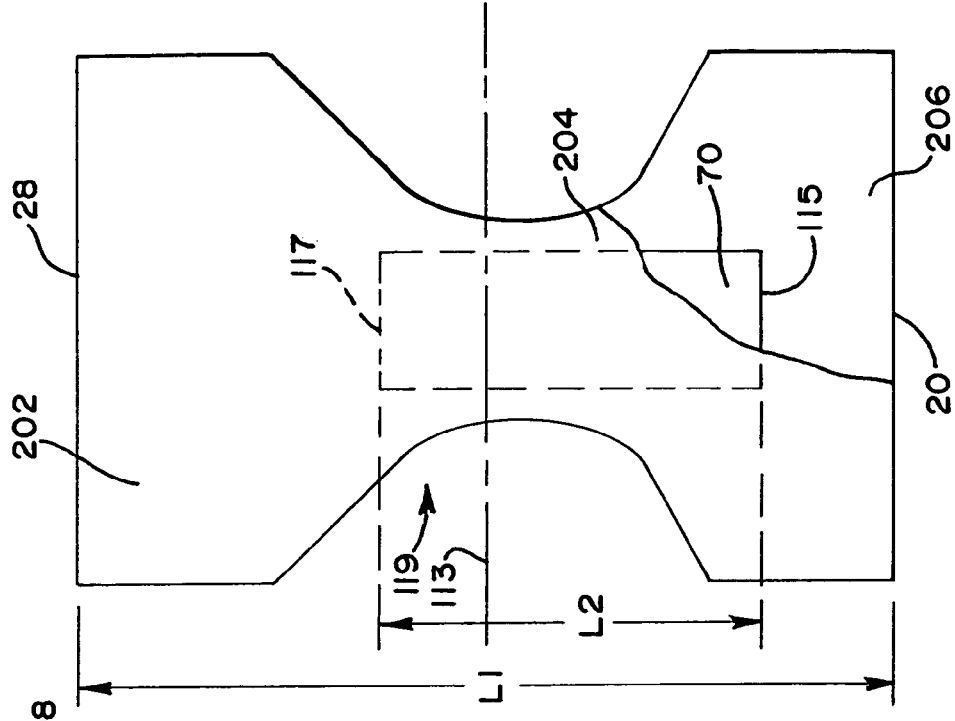
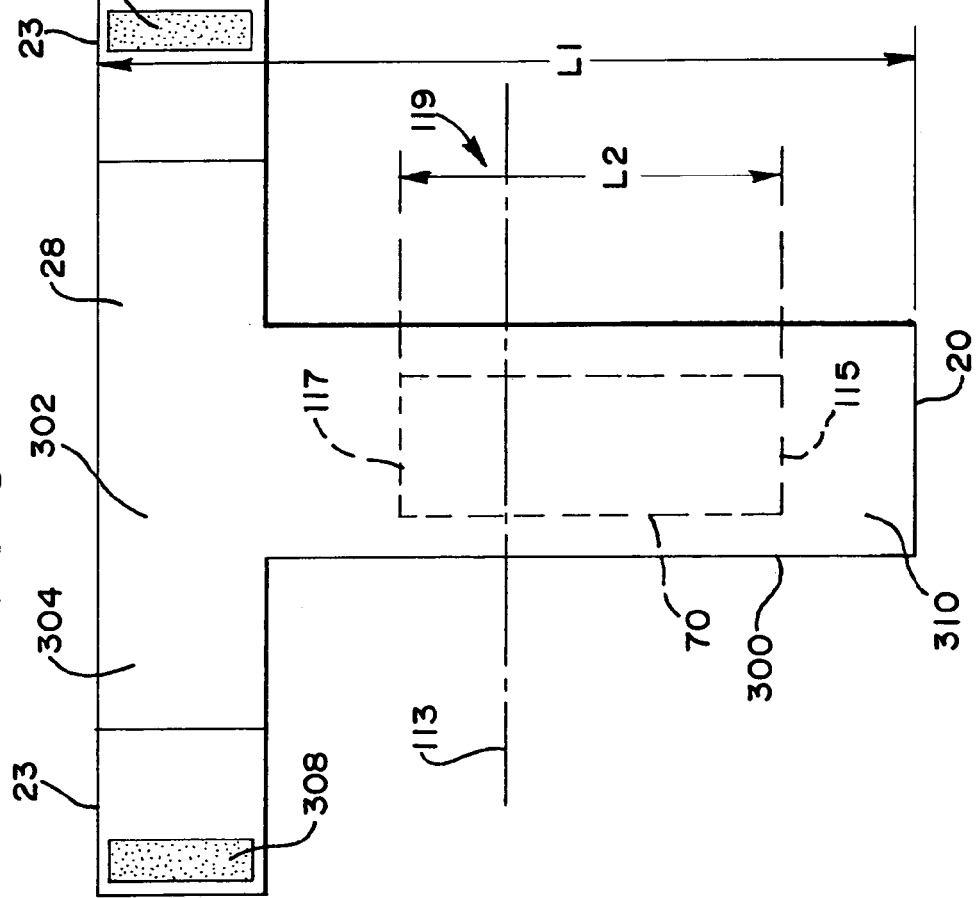

DISPOSABLE ABSORBENT UNDERGARMENT FOR MALES

BACKGROUND

The present invention relates generally to disposable undergarments, and in particular, to a disposable undergarment particularly suited for a male user.

Typically, incontinence garments are not designed specifically for male users. Rather, most incontinence garments, such as diapers or pant-type, pull-on garments, include an absorbent material that is positioned and sized to receive both urine and feces. Such types of garments are therefore designed to handle additional waste than what is necessary for most male users, especially males concerned primarily with urinary incontinence. In addition, urine emitted by males and females is directed to different areas of an undergarment, and garments targeted at females do not necessarily provide optimum coverage for male users. Consequently, such products may unnecessarily sacrifice comfort at an increased cost.

One solution for the particular problems associated with male incontinence is to provide an absorbent product that is held close to the male user's body with conventional, non-disposable underwear. Such products can be difficult to use with immobilized or bed-ridden users, however, where the application and removal of conventional underwear is made more difficult. In addition, the absorbent product is located by the user relative to the underwear and body, which can lead to suboptimal results if not properly positioned. Moreover, if the conventional underwear is inadvertently soiled, it must be washed or disposed of with additional costs and inconvenience associated therewith. In addition, the various layers of the absorbent product, in combination with the underwear, can provide a bulky appearance and reduce the overall comfort of the user.

SUMMARY

Briefly stated, in one aspect, a disposable absorbent garment includes a body chassis having a terminal front waist edge, a terminal back waist edge longitudinally spaced from the terminal front waist edge, a first length defined between the terminal front waist edge and the terminal back waist edge, and a laterally extending centerline defined half way between the terminal front and back waist edges. An absorbent insert is fixedly secured to the body chassis. The absorbent insert has a retention region including an absorbent material. The retention region has first and second longitudinally spaced boundaries and a second length defined between the first and second boundaries. The second length is less than or equal to 50% of the first length, and at least 70% of the second length is positioned between the centerline and the terminal front waist edge. There is no absorbent material disposed outside of the retention region defined between the first and second boundaries. In one embodiment, the body chassis is formed from separate front and rear body panels. A method of assembling a disposable absorbent garment is also provided.

The various aspects provide significant advantages over other disposable undergarments and methods. For example and without limitation, the forward positioning and smaller size (e.g., shorter length) of the retention region is ideally suited for male incontinence needs. At the same time, and due to the specific positioning of the absorbent insert, the proportion of absorbent material relative to the size of the overall garment can be reduced. Such reductions can result in substantial savings with respect to material costs. In addition, the absorbent garment is less bulky in the rear region, due to the lack of excess absorbent material, and thereby provides improved fit, comfort and appearance for the male user. Moreover, since the absorbent insert is fixedly secured to the body chassis, it is automatically located relative to the user's body by the application of the absorbent garment, thereby reducing the possibility that the absorbent insert will not be properly located.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

FIG. 1 is a plan view of one embodiment of an absorbent garment in an unfolded configuration with an absorbent insert connected to a bodyside surface of a front and rear body panel.

FIG. 2 is a cross sectional view of the absorbent garment shown in FIG. 1 taken along line 2-2.

FIG. 3 is a cross sectional view of the absorbent garment shown in FIG. 1 taken along line 3-3.

FIG. 4 is a cross-sectional view of the absorbent garment shown in FIG. 1 taken along line 4-4.

FIG. 5 is a plan view of another embodiment of an absorbent garment in an unfolded configuration with an absorbent insert connected to a bodyside surface of a front and rear body panel.

FIG. 6 is a plan view of another embodiment of an absorbent garment in an unfolded configuration with an absorbent insert connected to a garment side surface of a front and rear body panel.

DETAILED DESCRIPTION OF THE PRESENTLY PREFERRED EMBODIMENTS

It should be understood that the term "longitudinal," as used herein, means of or relating to length or the lengthwise direction 500. The term "laterally," as used herein, means situated on, directed toward or running from side to side in a direction 502 substantially perpendicular to the lengthwise direction.

The term "bodyside" should not be interpreted to mean in contact with the body of the user, but rather simply means the side that would face toward the body of the user, regardless of whether an undergarment is actually being worn by the user and regardless of whether there are or may be intervening layers between the component and the body of the user. Likewise, the term "garment side" should not be interpreted to mean in contact with the garments of the user, but rather simply means the side that faces away from the body of the user, and therefore toward any outer garments that may be worn by the user, regardless of whether the undergarment is actually being worn by a user, regardless of whether any such outer garments are actually worn and regardless of whether there may be intervening layers between the component and any outer garment.

The phrases "removeably attached," "removeably attaching," "removeably connected," "removeably engaged," "releasably attached," "releasably connected," or "releasably engaged," and variations thereof, refers to two or more elements being connected or connectable such that the elements tend to remain connected absent a separation force applied to one, both or all of the elements, and where the elements are capable of being separated upon the application of a separation force. The required separation force is typically beyond that encountered while wearing the absorbent garment.

The phrases "fixedly secured," "fixedly engaged," "fixedly attached," "fixedly connected," and variations thereof, refers to two or more elements being connected or connectable such that they are not disconnected or otherwise separated, and are not intended to be separated or disconnected by the end user, during the normal operation and use of the absorbent garment. Moreover, the separation of two elements being so connected is likely to damage or make unusable at least one of the two elements.

The terms "connecting," "coupled," "attached," and "secured," and variations thereof, broadly covers two or more items being directly connected one to the other, or by way of one or more intervening members or components.

Referring to FIGS. 1 and 4, an undergarment 2 includes a body chassis formed from a first, front body panel 4 and a second, rear body panel 6. The terms "body chassis" and "body panel" refers to the portion(s) of the undergarment, whether made of one or more layers or substrates or of one or more pieces or components, that is/are fitted circumferentially around at least a portion of the waist region of the user, including for example the user's lower back, buttock, hips and abdomen. The first and second body panels each have an inner, bodyside surface 10 and an outer, garment side surface 12. Referring to the embodiments of FIG. 1, the first, front body panel 4 has a first terminal crotch edge 14 forming a crotch portion 16 and leg opening portion 18 and a second terminal waist edge 20 which, in one embodiment, is linear but can assume other shapes. Likewise, the second, rear body panel 6 has a first terminal crotch edge 22 forming a crotch portion 24 and a leg opening portion 26 and a second terminal waist edge 28, which is shown linear but can assume other shapes. In various embodiments, the terminal crotch edges can be substantially linear, curvilinear, or have any other shape. For example and without limitation, the crotch portion and leg opening portions can form a generally sinusoidal curve, with one or both of the leg opening portions and/or crotch portions having a convex or concave contour. Of course, it should be understood that the crotch edge can have many forms and shapes not expressly disclosed herein. Each of the first and second body panels has an outboard side edge 30, 32 formed along the outer periphery of the opposite side portions of the first and second body panel. It should be understood that the outboard side edges of the front and rear body panels can have the same or different lengths relative to each other.

In one embodiment, a plurality, meaning two or more, elastic elements are secured to each of the first and second body panels. In preferred embodiment, a plurality of elastic elements are spaced across substantially the entire waist portion of the front and rear body panel 4, 6, although they may be spaced across a lesser length. For example, elastic elements can extend along the upper waist portion and along the lower terminal edge defining in part a leg opening 34.

In one embodiment, the front body panel has a "non-elasticized" area wherein there are no elastic elements, or other elastic or elastomeric backing members, incorporated therein or making up any portion of the thickness or cross-section of the body panel at that area. It should be understood, that in an alternative embodiment, one or more separate waist bands, with or without elastic elements, can be secured to one or both of the rear and front body panels, preferably along the upper terminal edges 20, 28 thereof. Likewise, one or more separate leg bands can be secured to one or both of the rear and front body panels along the leg open portions 18, 26 adjacent the leg openings 34. Alternatively, one or both of the body panels can be formed without any elastic elements. In other embodiments, the entirety of the front and/or rear body panels are elasticized.

The various waist and leg elastic elements can be formed from rubber or other elastomeric materials. One suitable material is a Lycra® elastic material. For example, the various elastic elements can be formed of Lycra® XA Spandex 540, 740 or 940 decitex T-127 or T-128 elastics available from E.I. duPont De Nemours and Company, having an office in Wilmington, Del.

Referring to FIGS. 3 and 4, each body panel 4, 6 is preferably formed as a composite, or laminate material, otherwise referred to as substrates or laminates, with an elastic core 136 sandwiched therebetween. In one embodiment, the elastic core 136 is made of an elastomeric film or nonwoven elastic or stretchable material including for example but not limited to styrenic copolymers of polyisoprene, polybutadiene or polyolefin, copolymers of polyolefins, natural or styrene butadiene rubber, polyurethanes, polyamides, polyesters, and co-extrusions/blends of the aforementioned materials. The elastic core 136 can be formed as a membrane or from the plurality of elastic strands 36, as described above. In one embodiment, two or more layers 40 are bonded to the elastic core 136, and/or each other, with various adhesives, such as hot melt, or by other techniques, including for example and without limitation ultrasonic bonding and heat pressure sealing. In one embodiment, the two layers are made of a nonwoven material such as a spunbond material, a bonded carded material or other known materials. In this way, the body panels are made of a stretchable/elastic material.

It should be understood that the body panels can be made of a single layer or substrate of non-woven material, a bi-layer substrate made of non-woven materials without an elastic core, or more than two layers or substrates. Of course, it should be understood that other knitted or woven fabrics, non-woven fabrics, elastomeric materials, polymer films, laminates and the like can be used to form one or more of the body panel layers. The term "non-woven" web or material, as used herein, means a web having a structure of individual fibers or filaments that are interlaid, but not in an identifiable manner and without the aid of textile weaving or knitting, as in a knitted or woven fabric.

In one embodiment, the body panel material can be secured to the elastic core, such as an elastomeric layer or elastic strands or ribbons, which have been elongated and retracted, such that the material is gathered when the elastic element(s) are relaxed. Alternatively, the material can be gathered and laminated to non-elongated elastic elements. In one preferred embodiment, the body panel includes a gathered elastic laminate made from nonwoven base sheets bonded with elongated elastic elements sandwiched therebetween.

In various preferred embodiments, the body panel material may be substantially permeable to air or substantially impermeable to air. The body panel material also may be substantially liquid-permeable or substantially liquid-impermeable. In particular arrangements, the body panel material may be substantially nonelastomeric. In other aspects, the body panels can include an elastomeric material that is elastomerically stretchable at least along one or both of the lateral article width and the longitudinal article length. Examples of such elastomeric composite materials can include a continuous filament stretch bonded laminate (CFSBL), a vertical filament laminate (VFL), neck-bonded-laminate (NBL), a stretch-bonded-laminate (SBL), a necked-stretch bonded laminate (NSBL) or a necked-thermal laminate, or the like, as well as combinations thereof. Exemplary CFSBL, NBL, SBL, and NSBL materials are described in U.S. Pat. Nos. 5,226,992, 4,981,747, 4,965,122, 5,336,545, 5,385,775, 5,514,470, 4,720,415, 4,789,699, 4,781,966, 4,657,802, 4,652,487, 4,655,760, 5,116,662 and 5,114,781, and 6,323, 389, all of which are hereby incorporated herein by reference. Exemplary VFL materials are described in U.S. Provisional Patent Application Ser. No. 60/204,307, filed May 15, 2000 and entitled "Method and Apparatus for Producing Laminated Articles," and PCT application WO 01/88245 A2, both assigned to Kimberly-Clark Worldwide, Inc., the Assignee of the present application, with the entire disclosures of both being hereby incorporated herein by reference. Such laminates can provide an improved combination of cloth-like feel and elastomeric stretchability. The body panels can be composed of materials that are elastic or elastomeric and exhibit biaxial stretch characteristics or lateral/longitudinal stretch characteristics, or which are extensible composites. Additional waist and leg elastic elements can be added to, but are not necessarily required by, the body panels. In one embodiment, the body panel can be made of a film or non-woven that is attached, by way of adhesives or thermal bonding, to an extensible non-woven material. Alternatively, the body panel can be made of a low modulus film such as ethylene methyl acrylate (EMA).

As shown in the embodiment of FIG. 1, the entirety of the body panels 4, 6, and portions of the crotch member 50, are elasticized, such that the entirety of each of the body panels can elongate and conform to the body of the user without any substantial spacing between the body panel and the user's body, and without the attendant bulkiness of a non-elasticized material.

In one embodiment, the body panels are breathable, cloth-like, multi-directional nonwoven laminates with stretch or extensible properties. In one embodiment, the non-woven layers are pre-necked, for example between about 10% and about 80%, in the longitudinal direction, which provides extensibility in the longitudinal direction with minimal force.

In one embodiment, the body panel members 4, 6 are made of non-woven laminates of two layers of 0.55 osy polypropylene spunbond material with elongated strands of Lycra® leg and waist elastics sandwiched between the spunbond layers and thereafter adhesively bonded. In other embodiments, two layers of 0.060 osy polypropylene spunbond material can be used. In one particular embodiment, the body panel is a nonwoven, wire-weave spunbond polypropylene fabric composed of about 1.6 denier fibers formed into a web having a basis weight of about 0.6 osy. One suitable nonwoven material is the Corinth 0.60 osy, 1.6 dpf wireweave, nonwettable Metallocene (EXXON ACHIEVE 2854 PP) spunbond material manufactured by Kimberly-Clark Corporation, the Assignee of the present application. In one embodiment, the body panel material is necked in the cross direction. As used herein, the term "necked," and variations thereof, refers to any material that has been constricted in at least one dimension by applying a tensioning force in a direction that is perpendicular to the desired direction of neck-down. Processes that may be used to constrict a material in such a manner include, for example and without limitation, drawing processes. The elastics are then elongated in the machine direction and secured to the body panel material. The elastics are then allowed to retract so as to gather the necked spunbond material in the lateral (machine) direction thereby creating an elastically gathered non-woven body panel with longitudinal extensibility. The term "gather," and variations thereof, as used herein means puckered, or contracted into folds or wrinkles, which should be understood as including micro-pleats.

In this way, the body panel can be elongated in both the longitudinal and lateral direction to conform to the body of the user when the garment is applied thereto. In particular, as the user pulls the garment up over their hips, the non-woven laminate body panels stretch in the lateral direction while the leg regions of the front and rear body panels conform to the crotch and body lines of the user. At the same time, the body panel material extends in the longitudinal direction to conform to the buttocks and stomach of the user. The extensibility of the body panels follows the natural curvature of user's body to provide conformance thereto. As the body panel extends in the longitudinal direction, the spacing between the laterally extending elastic elements, incorporated in one embodiment, will increase.

The body panel non-woven material is preferably substantially hydrophobic, which may optionally be treated with a surfactant or otherwise processed to impart a desired level of wettability and hydrophilicity.

It should be understood that an outer cover can be disposed over and secured to the front and rear body panels and crotch member of FIG. 1. In such an embodiment, the outer cover forms part of the overall body chassis and runs from the terminal waist edge of the front body panel to the terminal waist edge of the rear body panel. The outer cover can be made of any material, including the various non-woven, extensible and/or stretchable materials disclosed herein.

In another embodiment (not shown), the crotch edges of the front and rear body panels overlap and are joined one to the other, rather than being spaced apart, so as to form a "two-piece" body chassis (as opposed to a three-piece construction which utilizes a third crotch member piece, such as an absorbent insert, to form the chassis). The retention portion, which can be formed as two pieces, is sandwiched between layers of each of the front and rear body panels. Alternatively, the retention portion is formed as part of an absorbent insert that is secured to the bodyside surface of the joined front and rear body panels.

In another embodiment, shown in FIG. 6, the body chassis 202 includes a top sheet 204 and back sheet 206 that extend from the front to the rear terminal waist edges 20, 28 and form the body chassis, including front and rear bodypanels integrally joined with a crotch portion. The top sheet and back sheet can be made from any of the various materials disclosed herein. A retention portion 70 is disposed between the top sheet 204 and back sheet 206. Alternatively, a separate absorbent insert, including a retention portion disposed between a top sheet and a back sheet, is secured to the bodyside surface of the body chassis.

In yet another embodiment, shown in FIG. 5, a body chassis 302 has a T-shape, with a laterally extending waist portion 304 and a longitudinally extending crotch portion 306. The waist portion 304 wraps around the body of the user and is secured to a free end 310 of the crotch portion 306 that extends upwardly adjacent the front of the user, for example to the garment side surface of the crotch portion. The waist portion can be elasticized or not, and includes a pair of fasteners 308 secured to opposite sides thereof. The crotch portion can include a landing material suitable for engaging the fasteners. The waist portion defines both the rear waist edge 28, and the front waist edge 20 when wrapped around the user, while the end of the crotch portion can further define the front waist edge 20. It should be understood that the waist edge 20 defined by the crotch portion 306 does not necessarily have to be aligned with the waist edge 20 defined by the waist portion 304 when the garment is applied to the user. In one embodiment, the crotch portion 306 and the waist portion 304 are integrally formed from one or more layers and are continuous between the front and rear waist edges. In such an embodiment, a retention portion can be sandwiched, for example, between a continuous top sheet and back sheet. In another embodiment (not shown), the waist portion is formed as a separate belt, which is secured for example to an absorbent insert having one end connected thereto.

In yet another embodiment (not shown), a "five-piece" garment includes an absorbent insert that runs the length of the garment and has opposite ends that define the front and rear waist edges. Two pairs of side body panels, or ears, are connected to opposite sides of the absorbent insert adjacent opposite ends thereof. The lateral free edges of the side body panels can then be joined to form leg openings.

In yet another embodiment (not shown), the chassis, which can be formed from a top sheet and back sheet, is rectangular in shape, with the retention portion disposed between the top sheet and back sheet, or with a separate absorbent insert secured to the body side surface of the chassis. In this embodiment, the chassis can be pleated such that it can be expanded laterally outward to fit around the body of the user.

Referring to FIGS. 1 and 6, the crotch member 50 of the various undergarments, whether formed as a separate absorbent composite or formed in part by the body chassis, connecting the front and rear body panels 4, 6 can be folded such that the side edges 30, 32 of the front and rear body panels 4, 6 are aligned, whereinafter they can be fixedly secured at a seam to form the leg opening 34. The seam can be formed by bonding, sewing or otherwise attaching the side edges. Alternatively, the product can remain "open," wherein the body panels are releasably secured with one or more fastening members (not shown).

In one embodiment, the garment includes a combination of side edges that are secured to form a seam and fastening members that allow the fit of the undergarment to be adjusted. For example, in one embodiment, fastening members are preferably attached to the front body panel and extend inboard relative to the outboard side edge of the front body panel from an attachment location, which is preferably spaced inboard from the side edge. A landing member can be formed on or secured to the body panel to receive a refastenable portion of the fastening member. One or more lines of weakness can be provided along the front or rear body panel such that one or both of the body panels are breakable. The lines of weakness can comprise a perforation or other series of cuts, a thinning, breakage or separation of material, or a strip of a different kind of material bridging portions of the body panel that is more easily torn or broken than the other material thereof, which allow a user or the manufacturer to separate portions of the body panel. For example, the undergarment can be broken along the lines of weakness after the garment is applied to a user, or beforehand. In one embodiment, the fastening members are secured to the garment-side surface of the body panel.

It should be understood that, in other embodiments, the fastening members can be secured to the rear body panel and engage the front body panel or, conversely, can be secured to the front body panel and engage the rear body panel, preferably along at least a portion that is not elasticized. In one embodiment, the fastening members are fixedly secured to the outer, garment-side surface of the front and/or rear body panels, and releasably engage the outer, garment-side surface of the front and/or rear body panels, although it should be understood that the fastening members could be fixedly secured to an inner body-side surface of front and/or rear body panels and releasably engage an inner, body-side surface of the front and/or rear body panels.

When incorporated into a disposable absorbent undergarment, the fastening members can include a refastenable portion, such as an array of hook members, adhesives, such as pressure sensitive adhesives, buttons, zippers, snaps and other releasable and reattachable fastening devices. In various embodiments, the fastening member includes one, two or more than two tab members. In one embodiment, the fastening members comprise a carrier member, which is preferably fixedly secured to the side portions of the front body panel with adhesive bonds, sonic bonds, thermal bonds, pinning, stitching or other known types of attachment. In alternative embodiments, the fastening members can be fixedly secured to the rear body panel or to one or both of the front and rear body panels, for example, at the seam, as explained above.

Referring to the embodiments of FIGS. 1-4, the crotch member 50, otherwise referred to as an absorbent insert, is formed as a separate subassembly connected to either the bodyside or garment side surface 10, 12 of the body panel members 4, 6. Various garments having a "three-piece" construction including a front and rear body panel connected with an absorbent insert include for example and without limitation the Depend® Protective Underwear and Depend® Refastenable Underwear, both available from Kimberly-Clark Worldwide Corporation, the assignee of the present application. In either embodiment, the crotch member 50 has first and second opposed terminal end edges 60, 62. The crotch member 50 bridges the gap between the terminal edges 14, 22 of the body panels 4, 6 and is connected respectively to those body panels with an adhesive at adhesive regions.

In particular, the crotch member 50 has first and second end portions 102, 104 that overlap the front and rear body panels 4, 6 respectively and are connected thereto with the adhesive at the adhesive regions. In one embodiment, the entirety of the end portions 102, 104 of the crotch member that overlaps the body panels can be attached thereto. The crotch member 50 can be secured to the body panels when they are in a stretched or unstretched condition. The crotch member can be secured to the body panels. In other embodiments, only a portion of the crotch member are secured to the body panels. In the various embodiments, the adhesive region is formed by a continuous or intermittent swirl pattern, a line of adhesive, such as a bead, or a pattern of dots of adhesive.

In one embodiment, shown in FIGS. 1-4, the crotch member is configured as an absorbent insert 50 that includes a substantially liquid permeable top sheet 64, or liner, and a substantially liquid impermeable back sheet 66. A retention portion 70 is disposed or sandwiched between the topsheet and the backsheet, which are connected. It should be understood that the term "absorbent insert" refers to any material or assembly capable of absorbing liquids or bodily exudates, and may be formed from a single material or component, for example a retention portion, or can be formed as a composite of several components. An absorbent insert of this type of construction can be used in any of the one-piece, three-piece, T-shaped, five-piece or two-piece body chassis garments described above.

Referring to FIGS. 1-4, the top sheet 64, back sheet 66 and other components of the absorbent insert can be joined for example with adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or any array of lines, swirls or spots of construction bonds may be used to join the topsheet and backsheet, or any of the other components described herein.

In one embodiment, one or more crotch elastic members 38 are sandwiched between the top sheet 64 and backsheet 66 along the side edges thereof. The elastic members 38 can extend the entire longitudinal extent of the absorbent insert, or along only a portion thereof.

Additional layers, including for example, a liquid acquisition and distribution layer 72, also referred to as a surge or transfer layer, are also preferably incorporated into the absorbent insert. In one embodiment, the transfer layer does not run the entire length of the absorbent insert and is shorter than the retention portion.

In one embodiment, the retention portion 70, transfer layer 72 and other components, such as tissue layers, are free floating (unattached) between the back sheet 64 and the top sheet 66, which are secured along only the peripheral edges thereof. Alternatively, the retention portion 70, transfer layer 72 and other components are minimally attached to one or both of the back sheet 66 and top sheet 64. For example, the retention portion can be secured to the back sheet along an attachment location positioned along the longitudinal centerline 112 of the retention portion. Alternatively, or in combination with the back sheet connection, the transfer layer or retention portion can be minimally attached to the top sheet. In this way, the retention portion 70, transfer layer 72 and other components do not impede or substantially affect the lateral stretchability and extensibility of the absorbent insert 50 and in particular the top sheet and back sheet, at least one of which is secured to the body chassis.

In another alternative embodiment (not shown), the retention portion is secured along the centerline at a point midway between the two ends of the retention portion. In this embodiment, the retention portion also does not restrict or impede the stretchability and extensibility of the absorbent insert, and in particular the top sheet and back sheet, in the lateral or longitudinal directions 500, 502.

In other embodiments, the top sheet is indirectly joined to the backsheet by affixing the topsheet to intermediate layers, such as the surge layer or retention portion, which in turn is affixed to the backsheet. The absorbent insert also may include barrier cuffs, or leakage control shields, formed along the opposite longitudinally extending edges of the absorbent composite.

In one embodiment, the back sheet 66 is a stretchable, elastic, liquid impervious member. Alternatively, the back sheet may be liquid permeable, e.g., when an additional barrier layer is used with the retention portion. In one embodiment, shown in FIGS. 1-4, the back sheet 66 is a laminate structure made of a stretchable, elastic material, such as an elastomeric film 80, which is laminated to an extensible nonwoven material layer 82. It should be understood that the backsheet can be formed from a single layer or substrate or more than two layers or substrates. The backsheet can be stretchable in both the lateral and longitudinal direction, or be stretchable in one direction and extensible in the other.

The backsheet 66 prevents various bodily fluids and exudates from wetting or otherwise contaminating various bedding or outer garments worn by the user over the absorbent garment. The backsheet can be made of the same materials described above in connection with the body panels. In one embodiment, the backsheet can include a film, which can be made of the various materials described above.

The backsheet may include a micro-porous, "breathable" material which permits gases, such as water vapor, to escape from the absorbent garment while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance. In one embodiment, the absorbent insert includes a breathable stretch thermal laminate (BSTL).

In various embodiments, where a component, such as the backsheet is configured to be permeable to gas while having a resistance and limited permeability to aqueous liquid, the liquid resistant component can have a construction which is capable of supporting a selected hydrohead of water substantially without leakage therethrough. A suitable technique for determining the resistance of a material to liquid penetration is Federal Test Method Standard FTMS 191 Method 5514, 1978, or an equivalent thereof.

In one embodiment, the backsheet is sufficiently impermeable to liquid and semi-liquid materials to substantially prevent the undesired leakage of waste materials, defined as exudates, including for example urine and feces. For example, the backsheet member can desirably support a hydrohead of at least about 45 centimeters (cm) substantially without leakage. The backsheet member can alternatively support a hydrohead of at least about 55 cm, and optionally, can support a hydrohead of at least about 60 cm, or more, to provide improved benefits.

In one example, the backsheet can be composed of a necked fiber, a creped fiber, a micro-pleated fiber, polymer films or the like, as well as combinations thereof. The fabrics may be woven or nonwoven materials, such as spunbond fabrics.

In various constructions, the top sheet 64 can include various woven or nonwoven materials and laminates, which can be stretchable or extensible. In one embodiment, the top sheet 64, shown in FIGS. 1-4, is an extensible material, such as a necked spunbond material. For example, the topsheet can be composed of a meltblown or spunbonded web of desired fibers, and may also be a bonded-carded web. For example, the topsheet and liner can be made of a substantially hydrophobic material, and the hydrophobic material may optionally be treated with a surfactant or otherwise processed to import a desired level of wettability and hydrophilicity. In one particular embodiment of the invention, the topsheet is a nonwoven, spunbond polypropylene fabric composed of about 2.8-3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like. In another embodiment, the top sheet can also include an elastic material, such that it is stretchable.

The retention portion 70 is made of an absorbent material, which can be any material that tends to swell or expand as it absorbs exudates, including various liquids and/or fluids excreted or exuded by the user. For example, the absorbent material can be made of airformed, airlaid and/or wetlaid composites of fibers and high absorbency materials, referred to as superabsorbents. Superabsorbents typically are made of polyacrylic acids, such as FAVOR 880 available from Stockhausen, Inc. of Greensboro, N.C. The fibers can be fluff pulp materials, such as Alliance CR-1654, or any combination of crosslinked pulps, hardwood, softwood, and synthetic fibers. Airlaid and wetlaid structures typically include binding agents, which are used to stabilize the structure. In addition, various foams, absorbent films, and superabsorbent fabrics can be used as an absorbent material. Various acceptable absorbent materials are disclosed in U.S. Pat. No. 5,147,343 for Absorbent Products Containing Hydrogels With Ability To Swell Against Pressure, U.S. Pat. No. 5,601,542 for Absorbent Composite, and U.S. Pat. No. 5,651,862 for Wet Formed Absorbent Composite, all of which are hereby incorporated herein by reference. Furthermore, the proportion of high-absorbency particles can range from about 0 to about 100%, and the proportion of fibrous material from about 0 to about 100%. Additionally, high absorbency fibers can be used such as Oasis type 121 and type 122 superabsorbent fibers available from Technical Absorbent Ltd., Grimsby, Lincolnshire, United Kingdom.

In one embodiment, the retention portion suitably comprise a matrix of hydrophilic fibers, such as a web of cellulosic fluff, mixed with particles of superabsorbent material. In a particular embodiment, the retention portion 70 comprises a matrix of cellulosic fluff, such as wood pulp fluff, and superabsorbent hydrogel-forming particles. The wood pulp fluff may be exchanged with synthetic, polymeric, melt-blown fibers or with a combination of meltblown fibers and natural fibers. The superabsorbent particles may be substantially homogeneously mixed with the hydrophilic fibers or may be nonuniformly mixed. The fluff and superabsorbent particles may also be selectively placed into desired zones of the retention portion 70 to better contain and absorb body exudates. The concentration of the superabsorbent particles may also vary through the thickness of the retention portion. Alternatively, the retention portion 70 may comprise a laminate of fibrous webs and superabsorbent material or other suitable means of maintaining a superabsorbent material in a localized area.

As explained above, the retention portion may have any of a number of shapes, including for example and without limitation a rectangular shape, an I-shape (with enlarged end portions (see FIG. 1)), or a T-shape. It is generally preferred that the retention portion be narrower in the crotch area than in the front or rear portions of the garment. The size and the absorbent capacity of the retention portion 70 should be compatible with the size of the intended wearer and the liquid loading imparted by the intended use of the absorbent article. For example, the retention portion may have an enlarged end portion at the front body panel, for example T-shaped, when being used in garments designed for men. For example, in one embodiment, the enlarged end portion is at least 10% wider than a stem portion, and in another embodiment, at least 20% wider. In one embodiment, the retention portion is rectangular and has a width of from about 2 inches to about 8 inches.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces. Examples of synthetic, polymeric, high-absorbency materials include the alkali metal and ammonium salts of poly(acrylic acid) and poly(methacrylic acid), poly(acryla-mides), poly(vinyl ethers), maleic anhydride copolymers with vinyl ethers and alpha-olefins, poly(vinyl pyroli-done), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methylcellulose, carboxymethyl cellulose, hydroxypropyl cellulose, and the natural gums, such as alginates, xanthumgum, locust bean gum, and the like. Mixtures of natural and wholly or partially synthetic absorbent polymers can also be useful in the present invention. Such high-absorbency materials are well known to those skilled in the art and are widely commercially available. Other examples of superabsorbent polymers suitable for use in the present invention are Hysorb 8800 and SP-9394 polymers available from BASF Corp. located in Mount Olive, N.J. The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the retention portion 70. In one suitable embodiment, the retention portion contains at least 20% super absorbent material based on the total weight of the absorbent body, more suitably between about 20% and about 90% super absorbent material, even more suitably between about 30% and about 80% super absorbent material, and most suitable between about 40% and about 70% super absorbent material.

Optionally, a substantially hydrophilic tissue wrap-sheet (not illustrated) may be employed to help maintain the integrity of the airlaid fibrous structure of the retention portion. The tissue wrapsheet is typically placed about the retention portion over at least the two major facing surfaces thereof and composed of an absorbent cellulosic material, such as creped wadding or a high wet-strength tissue. In one aspect, the tissue wrapsheet can be configured to provide a wicking layer which helps to rapidly distribute liquid over the mass of absorbent fibers comprising the absorbent body. In another aspect, the wrapsheet material on one side of the absorbent fibrous mass may be bonded to the wrapsheet located on the opposite side of the fibrous mass.

The retention portion preferably can be made of a single or dual layer of absorbent material. The retention portion can include a folded or multi-layered configuration. Likewise, the entire absorbent insert can have a folded configuration, with various folds formed from one or more of the backsheet, top sheet, retention portion or other components. The retention portion can have a length substantially equal to, or slightly shorter than, the length of the absorbent insert. The retention portion can include one or more barrier layers attached to the absorbent material. In one embodiment, an upper tissue wrapsheet or substrate 74 is disposed adjacent the retention portion, with a lower tissue substrate 75 disposed adjacent an opposite side of the retention portion. Of course, as explained above, the tissue can completely envelope the retention position.

In one desired embodiment, the retention portion has a density in the range of 0.10 gm/cc to 0.50 gm/cc as measured using a circular 3-inch diameter platen applying 0.2 psi pressure.

In addition, in one desired embodiment, the superabsorbent material has a centrifuge retention capacity (CRC) in the range of at least about 20 grams liquid per gram weight of superabsorbent material, more suitably at least about 23 grams liquid per gram weight of superabsorbent material, still more suitably about 25 grams liquid per gram weight of superabsorbent material and even more suitably at least about 28 grams liquid per gram weight of superabsorbent material.

The Centrifuge Retention Capacity is defined by a Test that measures the ability of the gel particles (e.g., such as the surface treated absorbent material or the superabsorbent material prior to being surface treated) to retain liquid therein after being saturated and subjected to centrifugation under controlled conditions. The resultant retention capacity is stated as grams of liquid retained per gram weight of the sample (g/g). The sample to be tested is prepared from particles which are prescreened through a U.S. standard 30 mesh screen and retained on a U.S. standard 50 mesh screen. As a result, the sample comprises particles sized in the range of about 300 to about 600 microns. The particles can be prescreened by hand or automatically and are stored in a sealed airtight container until testing.

The retention capacity is measured by placing 0.2±0.005 grams of the prescreened sample into a water-permeable bag which will contain the sample while allowing a test solution (0.9 weight percent sodium chloride in distilled water) to be freely absorbed by the sample. A heat-sealable tea bag material, such as that available from Dexter Corporation of Windsor Locks, Conn., U.S.A., as model designation 1234T heat sealable filter paper works well for most applications. The bag is formed by folding a 5-inch by 3-inch sample of the bag material in half and heat-sealing two of the open edges to form a 2.5-inch by 3-inch rectangular pouch. The heat seals should be about 0.25 inches inside the edge of the material. After the sample is placed in the pouch, the remaining open edge of the pouch is also heat-sealed. Empty bags are also made to serve as controls. Three samples (e.g., filled and sealed bags) are prepared for the test. The filled bags must be tested within three minutes of preparation unless immediately placed in a sealed container, in which case the filled bags must be tested within thirty minutes of preparation.

The bags are placed between two Teflon® coated fiberglass screens having 3 inch openings (Taconic Plastics, Inc., Petersburg, N.Y.) and submerged in a pan of the test solution at 23 degrees Celsius, making sure that the screens are held down until the bags are completely wetted. After wetting, the samples remain in the solution for about 30±1 minutes, at which time they are removed from the solution and temporarily laid on a non-absorbent flat surface. For multiple tests, the pan should be emptied and refilled with fresh test solution after 24 bags have been saturated in the pan.

The wet bags are then placed into the basket of a suitable centrifuge capable of subjecting the samples to a g-force of about 350. One suitable centrifuge is a Heraeus LaboFuge 400 having a water collection basket, a digital rpm gauge, and a machined drainage basket adapted to hold and drain the bag samples. Where multiple samples are centrifuged, the samples must be placed in opposing positions within the centrifuge to balance the basket when spinning. The bags (including the wet, empty bags) are centrifuged at about 1,600 rpm (e.g., to achieve a target g-force of about 350), for 3 minutes. The bags are removed and weighed, with the empty bags (controls) being weighed first, followed by the bags containing the samples. The amount of solution retained by the sample, taking into account the solution retained by the bag itself, is the centrifuge retention capacity (CRC) of the sample, expressed as grams of fluid per gram of sample. More particularly, the retention capacity is determined as:

$$CRC = \frac{\text{sample/bag weight after centrifuge} - \text{empty bag weight after centrifuge} - \text{dry sample weight}}{\text{dry sample weight}}$$

The three samples are tested and the results are averaged to determine the centrifuge retention capacity (CRC). The samples are tested at 23±1 degrees Celsius at 50±2 percent relative humidity.

Referring to FIGS. 1, 5 and 6, the body chassis has a terminal front waist edge 20, a terminal back waist edge 28 longitudinally spaced from the terminal front waist edge and a first length L1 defined between the terminal front waist edge 20 and the terminal back waist edge 28. The body chassis further includes a laterally extending centerline 113 defined halfway between the terminal front and back waist edges 20, 28. The retention portion 70, which is formed from the absorbent material, defines a retention region 119. The retention region has first and second longitudinally spaced boundaries, defined by the first and second ends 115, 117 of the retention portion in one embodiment, and a second length L2 defined between the first and second boundaries. The second length L2 is less than or equal to 50% of the first length L1, and at least 70% of the second length L2 is positioned between the centerline 113 and the terminal front waist edge 20.

Moreover, in a desired configuration, there is no absorbent material disposed longitudinally outside of the retention region defined between the first and second boundaries 115, 117, meaning there is no absorbent material disposed between the first boundary 115 and the front waist edge 20, or between the second boundary 117 and the rear waist edge 28. Of course, it should be understood that the retention portion 70 can extend all of the way to the front waist edge 20, such that the front waist edge and the first boundary 115 are coextensive.

The combination of the size of the retention portion (less than or equal to 50% of the overall length of the garment) and the positioning thereof (at least 70% being positioned forward of the centerline 113) provides for a garment that is particularly well suited for male users. In this way, the retention portion can be made smaller and at less cost, yet still provide maximum protection for the male user. This is particularly true when the retention portion is made at least in part from superabsorbent materials, which have increased capacity over other types of absorbent materials.

In another aspect, the manufacturer or retailer of the aforedescribed absorbent garments provides instructional information to the user, for example by way of textual or pictorial indicia on the packaging materials, about how the garment works. For example, the manufacturer or retailer can explain to the end user the advantages of the variable adhesive regions, and the resultant advantages associated therewith.

Although the present invention has been described with reference to various embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A disposable absorbent garment comprising:
a body chassis having a terminal front waist edge, a terminal back waist edge longitudinally spaced from said terminal front waist edge, a first length defined between said terminal front waist edge and said terminal back waist edge, and a laterally extending centerline defined half way between said terminal front and back waist edges, wherein said body chassis is formed from a laminate structure having a plurality of layers, wherein all of said layers have the same length such that a thickness of said body chassis is the same along said length of said layers; and an absorbent insert fixedly secured to said body chassis, said absorbent insert comprising a retention region comprising an absorbent material, said retention region having first and second longitudinally spaced boundaries and a second length defined between said first and second boundaries, wherein said second length is less than or equal to 50% of said first length, wherein at least 70% of said second length is positioned between said centerline and said terminal front waist edge, and wherein there is no absorbent material disposed longitudinally outside of said retention region defined between said first and second boundaries.

2. The disposable absorbent garment of claim 1 wherein said absorbent insert comprises a single retention member defining said retention region, said retention member having first and second ends corresponding to said first and second boundaries.

3. The disposable absorbent garment of claim 1 wherein said absorbent material comprises a superabsorbent material.

4. The disposable absorbent garment of claim 3 wherein said superabsorbent material forms at least 20% of the absorbent material by weight.

5. The disposable absorbent garment of claim 3 wherein said superabsorbent material has a centrifuge retention capacity of at least 20 grams liquid per gram weight of superabsorbent material.

6. A disposable absorbent garment comprising:

a body chassis having a terminal front waist edge, a terminal back waist edge longitudinally spaced from said terminal front waist edge, a first length defined between said terminal front waist edge and said terminal back waist edge, and a laterally extending centerline defined half way between said terminal front and back waist edges, wherein said body chassis is formed from a laminate structure having a plurality of layers, wherein all of said layers have the same length such that a thickness of said body chassis is the same along said length of said layers; and an absorbent insert fixedly secured to said body chassis, said absorbent insert comprising a retention region comprising an absorbent material, wherein said absorbent material comprises a superabsorbent material, said retention region having first and second longitudinally spaced boundaries and a second length defined between said first and second boundaries, wherein said second length is less than or equal to 50% of said first length, wherein at least 70% of said second length is positioned between said centerline and said terminal front waist edge, wherein there is no absorbent material disposed longitudinally outside of said retention region defined between said first and second boundaries, and wherein said retention portion has a density between about 0.10 gm/cc and about 0.50 gm/cc.

7. The disposable absorbent garment of claim 1 wherein said body chassis comprises a front body panel comprising said terminal front waist edge and a terminal crotch edge longitudinally spaced from said terminal front waist edge, and a rear body panel comprising said terminal back waist edge and a terminal crotch edge longitudinally spaced from said terminal back waist edge, said terminal crotch edges of said front and rear body panels being longitudinally spaced to form a gap therebetween, and wherein said absorbent insert comprises first and second longitudinally spaced end portions and opposite laterally spaced side edges, wherein said absorbent insert bridges said gap between said front and rear body panels with said first and second end portions overlying and connected to said front and rear body panels respectively.

8. The disposable absorbent garment of claim 1 wherein said body chassis comprises a non-woven material.

9. The disposable absorbent garment of claim 8 wherein said body chassis further comprises an elastic material, wherein said body chassis is stretchable in at least a lateral direction.

10. The disposable absorbent garment of claim 1 further comprising at least a pair of fasteners positioned at one end of said body chassis on opposite sides thereof, wherein said at least said pair of fasteners releasably engages an opposite end of said body chassis on said opposite sides thereof with a pair of leg openings being defined at least in part by said body chassis.

11. A disposable absorbent garment comprising:

a front body panel comprising a terminal waist edge and a terminal crotch edge;

a rear body panel comprising a terminal waist edge and a terminal crotch edge, wherein said terminal crotch edge of said rear body panel is longitudinally spaced from and forms a gap with said terminal crotch edge of said front body panel, and wherein a first length is defined between said terminal waist edge of said front body panel and said terminal waist edge of said rear body panel, and wherein a laterally extending centerline is defined half way between said terminal waist edges of said front and rear body panels; and an absorbent insert comprising first and second longitudinally spaced end portions each having a terminal edge and opposite laterally spaced side edges, wherein said absorbent insert bridges said gap between said front and rear body panels with said first and second end portions overlying and connected to said front and rear body panels respectively and with said terminal edges of said first and second end portions longitudinally spaced from said terminal waist edges of said front and rear body panels respectively and with said terminal edges of said first and second end portions longitudinally spaced from said terminal crotch edges of said front and rear body panels respectively, said absorbent insert comprising a retention member formed from an absorbent material, said retention member having first and second longitudinally spaced ends and a second length defined between said first and second ends, wherein at least 70% of said second length is positioned between said centerline and said terminal waist edge of said front body panel, and wherein there is no absorbent material disposed longitudinally outside of said retention region defined between said first and second boundaries.

12. The disposable absorbent garment of claim 11 wherein said second length is less than or equal to 50% of said first length.

13. The disposable absorbent garment of claim 11 wherein said absorbent material comprises at least 20% superabsorbent material by weight.

14. The disposable absorbent garment of claim 11 wherein each of said front and rear body panels comprises a non-woven material.

15. The disposable absorbent garment of claim 14 wherein each of said front and rear body panels further comprises an elastic material, wherein each of said front and rear body panels are stretchable in at least a lateral direction.

16. The disposable absorbent garment of claim 11 further comprising at least a pair of fasteners connected to one of said front and rear body panels, wherein said at least said pair of fasteners releasably engages the other of said front and rear body panels.

17. A method of assembling a disposable absorbent garment comprising:
providing a body chassis having a terminal front waist edge, a terminal back waist edge longitudinally spaced from said terminal front waist edge, a first length defined between said terminal front waist edge and said terminal back waist edge, and a laterally extending centerline defined half way between said terminal front and back waist edge, wherein said body chassis is formed from a laminate structure having a plurality of layers, wherein all of said layers have the same length such that a thickness of said body chassis is the same along said length of said layers; and
fixedly securing an absorbent insert to said body chassis, wherein said absorbent insert comprising a retention region comprising an absorbent material, said retention region having first and second longitudinally spaced boundaries and a second length defined between said first and second boundaries, wherein said second length is less than or equal to 50% of said first length, wherein at least 70% of said second length is positioned between said centerline and said terminal front waist edge, and wherein there is no absorbent material disposed outside of said retention region defined between said first and second boundaries.

18. The method of claim 17 wherein said absorbent insert comprises a single retention member defining said retention region, said retention member having first and second ends corresponding to said first and second boundaries.

19. The method of claim 17 wherein said absorbent material has at least 20% superabsorbent material by weight.

20. A method of assembling a disposable absorbent garment comprising:
providing a body chassis having a terminal front waist edge, a terminal back waist edge longitudinally spaced from said terminal front waist edge, a first length defined between said terminal front waist edge and said terminal back waist edge, and a laterally extending centerline defined half way between said terminal front and back waist edge; and
fixedly securing an absorbent insert to said body chassis, wherein said absorbent insert comprising a retention region comprising an absorbent material, said retention region having first and second longitudinally spaced boundaries and a second length defined between said first and second boundaries, wherein said second length is less than or equal to 50% of said first length, wherein at least 70% of said second length is positioned between said centerline and said terminal front waist edge, and wherein there is no absorbent material disposed outside of said retention region defined between said first and second boundaries;
wherein said body chassis comprises a front body panel comprising said terminal front waist edge and a terminal crotch edge longitudinally spaced from said terminal front waist edge, and a rear body panel comprising said terminal back waist edge and a terminal crotch edge longitudinally spaced from said terminal back waist edge, said terminal crotch edges of said front and rear body panels being longitudinally spaced to form a gap therebetween, and wherein said absorbent insert comprises first and second longitudinally spaced end portions each having a terminal edge and opposite laterally spaced side edges, and wherein said fixedly securing said absorbent insert to said body chassis comprises bridging said gap between said front and rear body panels with absorbent insert wherein said first and second end portions overlie said front and rear body panels respectively, and fixedly securing said first and second end portions to said front and rear body panels respectively with said terminal edges of said first and second end portions longitudinally spaced from said terminal waist edges of said front and rear body panels respectively and with said terminal edges of said first and second end portions longitudinally spaced from said terminal crotch edges of said front and rear body panels respectively.

21. The method of claim 17 wherein said body chassis comprises a non-woven material.

22. The method of claim 21 wherein said body chassis further comprises an elastic material, wherein said body chassis is stretchable in at least a lateral direction.

23. The method of claim 17 further comprising providing at least a pair of fasteners positioned at one end of said body chassis on opposite sides thereof, wherein said at least said pair of fasteners are releasably engageable with an opposite end of said body chassis on said opposite sides thereof.

* * * * *